United States Patent [19]

Tipton

[11] Patent Number: 5,555,892
[45] Date of Patent: Sep. 17, 1996

[54] BIOPSY SHAVER

[76] Inventor: Clyde C. Tipton, 3820 Hunt Rd. #119, Tampa, Fla. 33614

[21] Appl. No.: 339,415

[22] Filed: Nov. 14, 1994

[51] Int. Cl.⁶ ..................................... A61B 17/32
[52] U.S. Cl. .......................................... 128/757; 128/749
[58] Field of Search .................... 128/749, 751, 128/757; 606/131, 132, 133, 160, 172

[56] References Cited

U.S. PATENT DOCUMENTS

| | | | |
|---|---|---|---|
| 1,174,932 | 3/1916 | Grenier | 606/132 X |
| 3,013,553 | 12/1961 | Averbach | 128/751 |
| 3,327,702 | 6/1967 | DeMarco | 128/751 |
| 4,038,986 | 8/1977 | Mahler | 606/132 |
| 4,338,952 | 7/1982 | Augros | 128/751 X |
| 4,438,767 | 3/1984 | Nelson | 128/160 X |
| 4,943,295 | 7/1990 | Hartlaub et al | 606/131 |
| 5,196,020 | 3/1993 | Atkinson et al. | 606/131 X |

FOREIGN PATENT DOCUMENTS

| | | | |
|---|---|---|---|
| 482831 | 7/1954 | Italy | 606/131 |

*Primary Examiner*—Sam Rimell

[57] ABSTRACT

An improved biopsy shaver for removing cutaneous specimens from the surface of the skin comprising a thin flexible blade, a thin flexible plastic body, a pair of angled flaps, a measuring ruler, and a plurality of raised ridges attached to the angled flaps. The angled flaps are positioned in a upward fashion to assure that the blade will be bent in a downward fashion when the angled flaps are squeezed together. A plurality of raised ridges are provided that will allow the practitioner to have a firm hold on the angled flaps when performing a biopsy. An additional measuring ruler is provided to allow the practitioner to measure cutaneous specimens prior to removal.

3 Claims, 2 Drawing Sheets

BIOPSY SHAVER

BACKGROUND OF INVENTION

1. Field of the Invention

This invention is related to the field of surgical cutting of cutaneous specimens. More specifically, the present invention disclosed herein is an improved version of a biopsy shaver with unique advantages.

2. Description of the Prior Art

Several years ago, the razor blade was introduced as an alternative device for performing shave removal and/or biopsy of skin lesions. Though inexpensive and readily available, the razor blade is somewhat cumbersome to use and poses a risk for accidental injury to the practitioner. Herein, the disclosed invention is an improved modification of this procedure utilizing an innovative adaptor designed to facilitate the safe and effective use of the razor blade in dermatologic practice.

For many years, the razor blade has been a commonly employed device for obtaining skin specimens. One of the earliest reports of the razor blade biopsy technique was in 1936, when Buhmann utilized the razor blade to secure superficial cutaneous samples for the purpose of researching epidermal metabolism. Since this time, several practitioners have commented on the versatility of this instrument. Razor blades have been utilized in curettage devices, e.g., Razor Curette, as well as for the purpose of obtaining epidermal specimens for examining hyphae and dermal specimens to obtain fibroblasts for culture.

Besides its wide array of adaptable uses, the razor blade has several other advantages. Shelly W., describes some of these in his evaluation of the razor blade's role in dermatologic practice. He notes that the razor blade served as a precise way in which to obtain cutaneous specimens in a simple and cost effective manner. He further acknowledges the razor blade's superior cutting edge to that of a scalpel blade and the ease in which one can perform multiple and serial biopsies. Finally, Shelly comments on the advantages of the blade being readily flexible, disposable and its ability to remove in total, a wide array of lesions such as bullae or nevi that may occur in areas hard to access, e.g., scrotum, interdigital web, concha.

The disadvantages of the typical razor blade is that there are several features inherent to the device which make it less attractive. Though flexible in nature, the razor blade is often cumbersome for the practitioner to use. The sharp edges of the blade as well as the limited contact of the forefinger and thumb with the side blade make biopsy procedures uncomfortable to perform and sometimes difficult. Thus, the practitioner may feel somewhat awkward with this device and endure a risk of accidental injury, especially if he or she has limited experience or suffers from certain rheumatologic or neurologic conditions, e.g. practitioners with arthritis who routinely perform skin biopsies. Blade breakage, unintentional or intentional, can also be a cause of injury, e.g. laceration, bleeding. The intentional breakage of one blade to obtain two cutting blade edges can be a difficult and time consuming chore. Finally, the razor blade can be a less professional appearing and more intimidating way of performing biopsies, especially in the case of young children or those who are afraid of instruments that readily appear sharp.

One approach provided for has been in the art of Hartlaub of U.S. Pat. No. 4,943,295 wherein the abstract illustrates "A surgical cutting tool that may be used in cutting away protuberances from the skin of an individual includes a thin flexible blade including two side margins and a front margin which is keen-edged, and two finger grips which each include an engagement surface affixed to and extending along one side margin of the blade, and an outwardly facing griping surface so that the tool can be held by the finger grips and thereby safely, easily and comfortably bent into an arcuate shape for cutting by bringing the finger grips closer together. Preferably each gripping surface forms a rounded notch conforming in approximate shape to a finger. The gripping surface forming the notch may include gripping protrusions which enable a user's fingers to grip the tool by the finger grips firmly. The toll preferably includes a sheathlike guard formed from flexible material which is affixed to and extends along and covers a rear margin of the blade between the finger grips. Although the guard protects a user of the tool from the keen-edged blade rear margin, the flexible material from which it is formed allows the user to bend the blade without substantial resistance from the guard." A shortcoming to this approach is that when the user applies pressure to the finger grips, the blade can bend or flex in either an upwards or downwards fashion. The user must use an additional finger to apply pressure to the top center of the blade to make sure that the blade is bent in a downward fashion, thus increasing the level of operating difficulty.

While some of the prior arts contain similarities of the invention disclose herein, none of them teach or suggest all of the advantages of the present invention.

SUMMARY OF THE INVENTION

A new design for an improved biopsy shaver is introduced to address those problems inherent to the standard blade instrument. The improved biopsy shaver typically employs a super stainless blade measuring 0.0004 inches in thickness which is embedded in a FDA approved flexible, polypropylene plastic polymer measuring. The polymer is constructed of a non-inflammable material and contains a dye (blue) which is also FDA approved for medical usage. The improved biopsy shaver is composed of one unit which is readily disposable and priced compatibly with the standard 15 blade scalpel instrument.

There are several advantages of the improved biopsy shaver instrument compared to the standard razor blade. One of the most readily apparent improvements in the design is in the adaptor plastic side guard structure. The guard wall enhances practitioner comfort by avoiding digit contact with sharp metal. This device further allows for greater control of the biopsy shaver with the forefinger. The resultant enhanced stability and comfort may serve to reduce the risk of accidental injury secondary to operator inexperience or physical impairment, e,g. arthritis.

The blade being melded into the plastic helps to avoid accidental springing or projectile motion of the sharp cutting edge. This serves to further reduce the risk of injury. It is important to recognize that blade flexibility is maintained with the polypropylene polymer and the control of biopsy depth is easily achieved. This biopsy shaver is believed to have the same advantages of the standard razor blade instrument with the addition of having a more professional and less intimidating appearance for the patient. Finally, the unit is readily disposable, priced compatible with the standard 15 scalpel blade, and is already in one piece, thereby saving time and needless worry from breaking one razor blade into two cutting edges.

Accordingly, it is an object of this invention to provide an improved biopsy shaver that will enhance the comfort level to the practitioner. This will allow the practitioner to work for longer periods of time while being able to concentrate more fully on the biopsy of cutaneous specimens.

A further object of this invention is to provide an improved biopsy shaver having angled side flaps that will assist the practitioner in bending the cutting blade in a downward fashion. These angled flaps, by design, will force the blade in a downward fashion when the angled flaps are squeezed together by the practitioner's fingers.

Another object of this invention to provide an improved biopsy shaver having side flaps with a gripping means to decrease the risk of accidental injury to the practitioner and patient. The gripping means assures the practitioner of a firm grip and therefore decreases accidents occurring from slippage.

A further object of this invention is to provide an improved biopsy shaver having a one piece design to save time for the practitioner.

Still another object of this invention is to provide an improved biopsy shaver having disposable capabilities. This will assure the patient that the practitioner is not using an old, possibly contaminated biopsy shaver but rather a new sharp and sterile biopsy shaver.

Still yet another object of this invention is to provide an improved biopsy shaver having a more professional appearance and less intimidating manner in which to obtain cutaneous specimens.

A further object of this invention is to provide an improved biopsy shaver with a measuring ruler built therein the plastic body.

In carrying out this invention in the illustrative embodiment thereof, an improved biopsy shaver is held by at least two fingers of a practitioner at the two lateral angled flaps provided by the biopsy shaver. If needed, the biopsy shaver can be bent downward with a further finger in a concave fashion. This will allow the cutting edge of the biopsy shaver to focus on a more specific area of cutting rather than a broad area of cutting. The practitioner than removes cutaneous specimens as needed with the cutting edge of the biopsy shaver.

BRIEF DESCRIPTION OF THE DRAWINGS

This invention, together with other objects, features, aspects and advantages thereof, will be more clearly understood from the following description, considered in conjunction with the accompanying drawings.

Two sheets of drawings are furnished, sheet one contains FIG. 1 and FIG. 2.

Figure 3:
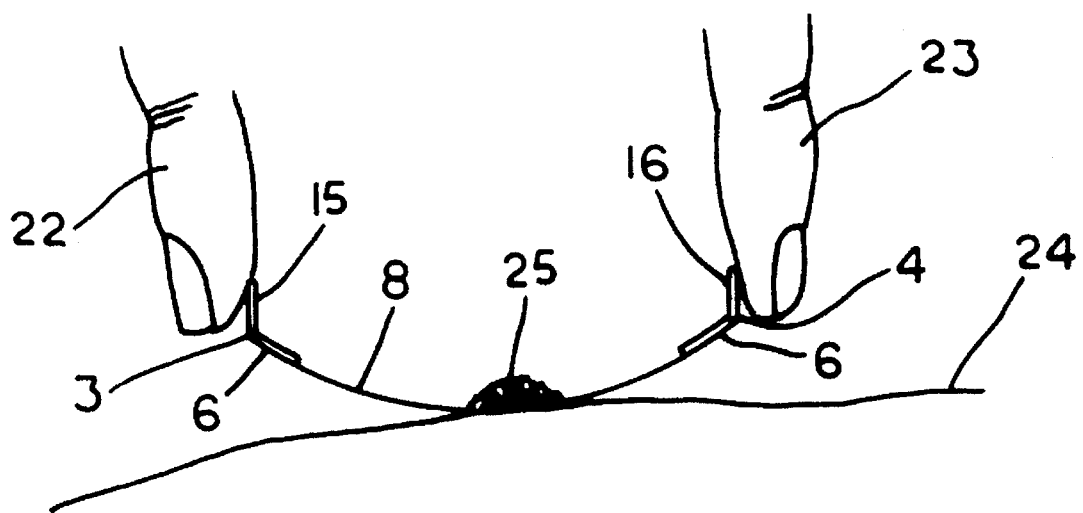

Sheet two contains FIG. 3, a frontal side view of the biopsy shaver in the process of removing a protruding object from the skin surface.

DESCRIPTION OF THE PREFERRED EMBODIMENTS

Figure 1:
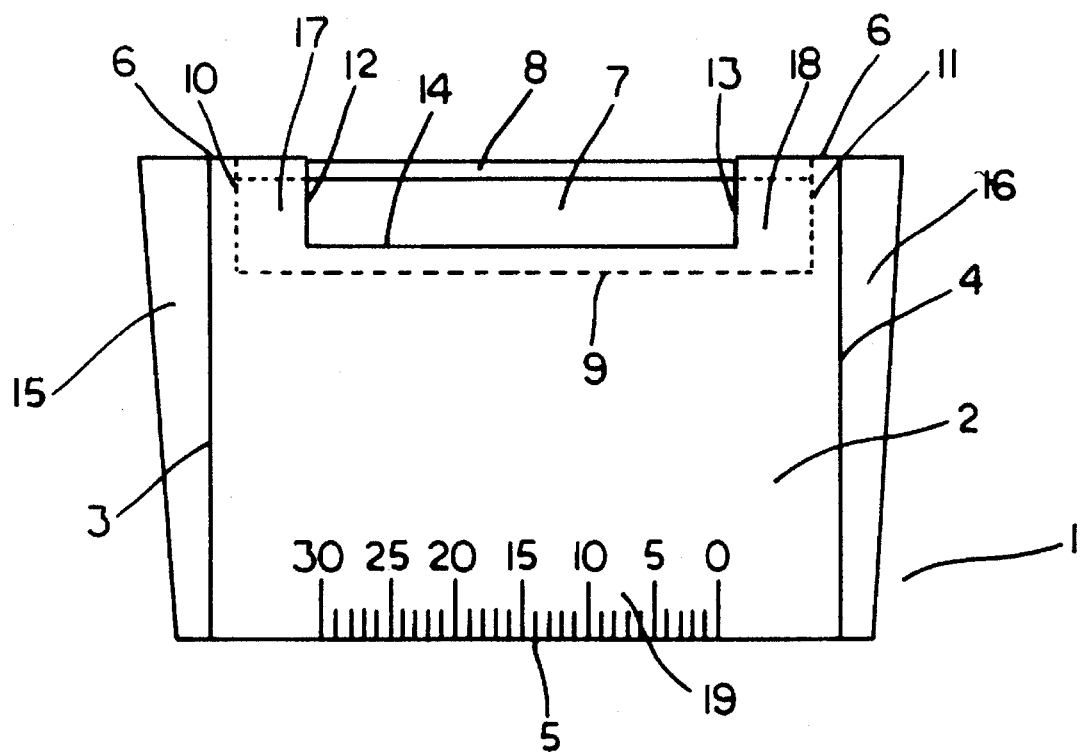
FIG. 1 is a top view of the biopsy shaver showing the lateral angled flaps, the cutting blade, the measuring ruler, and the plastic body.

Referring now to FIG. 1, a biopsy shaver referred to generally by the reference numeral 1 is made of a plastic body 2. The plastic body 2 having a substantially rectangular body with two lateral sides 3 and 4, a rear side 5 and a front side 6. The front side 6 of the plastic body 2 having a substantially rectangular cavity affixed therein. The rectangular cavity having three sides comprising a rear side 14 and two lateral sides 12 and 13.

The plastic body 2 having a measuring ruler 19 affixed thereto and aligned with the rear side 5. Additionally, the plastic body 2 having a pair of lateral angled flaps 15 and 16 affixed thereto the sides 3 and 4 of the plastic body 2 respectively.

Referring to the front side 6 of the plastic body 2 is a blade 7 embedded therein the rectangular cavity. The blade 7 having a substantially square body with a rear side 9, two lateral sides 10 and 11, and a front keen-edged side 8. The keen-edge side 8 is the portion of the blade used to remove cutaneous specimens from the skin. Portions of the blade 17 and 18 are embedded into the plastic body 2 for a secured fit.

Figure 2:
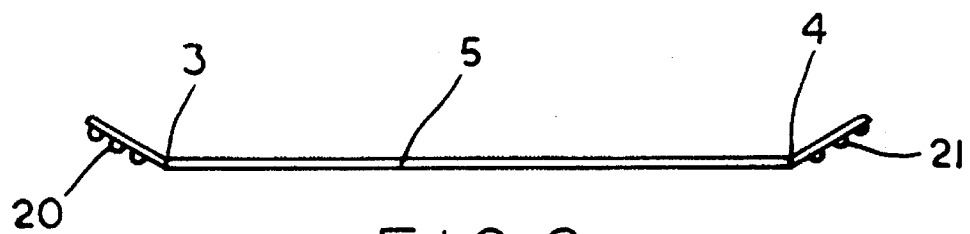
FIG. 2 shows a rear side view of the biopsy shaver accentuating the raised ridges protruding from the lateral angled flaps.

Referring now to FIG. 2, we see a rear side view of the biopsy shaver 1 showing the rear side 5. The plastic body 2 with a pair of angled flaps 15 and 16 affixed thereto the sides 3 and 4 respectively. The angled flaps 15 and 16 are provided to assure the practitioner that when the flaps are squeezed together, the blade 7 will always bend in a downward fashion. The angled flaps 15 and 16 having a plurality of parallel raised ridges 20 and 21 affixed thereto respectively. These raised ridges serve to provide a means of additional friction or gripping means between the practitioner's fingers and the angled flaps.

Finally, referring to FIG. 3, we see a front side view of the biopsy shaver 1 in a bowed or bent position ready to remove a protrusion 25 from a skin surface 24. FIG. 3 showing the keen-edge 8 cutting into the protrusion 25 for removal. A pair of fingers 22 and 23 are shown gripped onto angled flaps 15 and 16 respectively. The angled flaps 15 and 16 being affixed to sides 3 and 4 respectively. The biopsy shaver 1 is bent in a downward position when the angled flaps are squeezed together. The angle in the angled flaps assures that the biopsy shaver will be bent in the downward position every time the angled flaps are squeezed together.

Accordingly, a very unique, attractive, and convenient apparatus are provided for an improved biopsy shaver to obtain cutaneous specimens.

Since minor changes and modifications varied to fit particular operating requirements and environments will be understood by those skilled in the art, the invention is not considered limited to the specific examples chosen for purposes of illustration, and includes all changes and modifications which do not constitute a departure from the true spirit and scope of this invention as claimed in the following claims and reasonable equivalents to the claimed elements.

What is claimed is:

1. A surgical cutting tool for removing cutaneous specimens from the skin, said cutting tool comprising:

(a) a thin flexible blade having a substantially rectangular body with two lateral sides, a rear side, and a front side with a keen-edge;

(b) a thin flexible plastic body having two lateral sides, a rear side, a front side, a top surface, and a bottom surface, said front side having a substantially rectangular cavity to accept said blade, said blade being embedded thereto said cavity, said blade having said front keen-edge being exposed from said plastic body;

(c) a pair of straight flaps affixed to said lateral sides of said plastic body, said flaps being angled upwardly relative to said top surface of said plastic body whereby the angle between said flaps and said top surface is greater than ninety degrees but less than one hundred and eighty degrees.

2. A surgical cutting tool as set forth in claim 1 wherein a gripping means is affixed thereon said flaps.

3. A surgical cutting tool asset forth in claim 1 wherein a measuring ruler is affixed thereon said top surface said plastic body.

* * * * *